United States Patent [19]

Jaedicke et al.

[11] 4,256,643
[45] Mar. 17, 1981

[54] 3-CHLORO-3-METHYL-BUTANE-1,4-DIAL-BIS-ACETALS AND 3-METHYL-BUT-2-ENE-1,4-DIAL-BIS-ACETALS, A PROCESS FOR THE PREPARATION OF THESE COMPOUNDS AND THEIR USE

[75] Inventors: Hagen Jaedicke, Ludwigshafen; Joachim Paust, Neuhofen, both of Fed. Rep. of Germany

[73] Assignee: BASF Aktiengesellschaft, Fed. Rep. of Germany

[21] Appl. No.: 76,412

[22] Filed: Sep. 17, 1979

[30] Foreign Application Priority Data

Sep. 30, 1978 [DE] Fed. Rep. of Germany ....... 2842715

[51] Int. Cl.$^3$ ............................................ C07D 319/04
[52] U.S. Cl. ................................................. 260/340.7
[58] Field of Search ....................................... 260/340.7

[56] References Cited

U.S. PATENT DOCUMENTS

| 3,671,590 | 6/1972 | Wiese et al. ............... 260/586 R X |
| 4,120,868 | 10/1978 | Jaedicke et al. ................. 260/340.7 |

FOREIGN PATENT DOCUMENTS

| 2357752 | 6/1975 | Fed. Rep. of Germany ........ 260/340.7 |
| 2513999 | 10/1976 | Fed. Rep. of Germany ........ 260/340.7 |
| 1422684 | 1/1976 | United Kingdom .................. 260/340.7 |
| 529170 | 7/1975 | U.S.S.R. ................................ 260/340.7 |

OTHER PUBLICATIONS

Chem. Abstracts, vol. 62, 6396h.
Chem. Abstracts 86, 106678t.
Chem. Abstracts 65, 7853r.
Chem. Abstracts–8th Coll. (m–dioxane-2,2'-vinylenebis derivs.)

*Primary Examiner*—Ethel G. Love
*Attorney, Agent, or Firm*—Keil & Witherspoon

[57] ABSTRACT

3-Chloro-3-methyl-butane-1,4-dial-bis-acetals and 3-methyl-but-2-ene-1,4-dial-bis-acetals are obtained by reacting a six-membered cyclic acetal of 3-methyl-but-3-en-1-al with an alkyl nitrite in the presence of methanol and hydrogen chloride and, if desired, eliminating HCl in the conventional manner.

The butanedial-bis-acetals and butenedial-bis-acetals are valuable intermediates through which the trans-3-methyl-but-2-ene-1,4-dial-1-acetals, which are sought-after products for terpene syntheses, can be obtained in an industrially particularly advantageous manner.

3 Claims, No Drawings

3-CHLORO-3-METHYL-BUTANE-1,4-DIAL-BIS-ACETALS AND 3-METHYL-BUT-2-ENE-1,4-DIAL-BIS-ACETALS, A PROCESS FOR THE PREPARATION OF THESE COMPOUNDS AND THEIR USE

The present invention relates to butanedial-bis-acetals and butenedial-bis-acetals of the general formula I

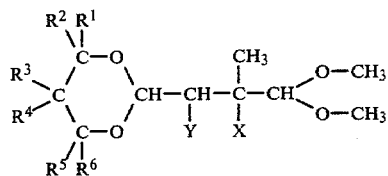

where $R^1$ to $R^6$ are H, —$CH_3$ or —$C_2H_5$, preferably H or —$CH_3$, but preferably only from 1 to 4 of the radicals $R^1$ to $R^6$ are —$CH_3$ and the remainder are —H, and Y is H if X is Cl (Ia) or Y and X together are a further bond between the carbon atoms bearing Y and X (Ib), to a process for their preparation and to their use for the preparation of 3-methyl-fumarodialdehyde-1-monoacetals (trans-3-methyl-but-2-ene-1,4-dial-1-acetals), which are sought-after compounds for terpene syntheses.

The trans-3-methyl-but-2-ene-1,4-dial-1-monoacetals are of great importance since they may be used to carry out successive Wittig reactions to give innumerable compounds of biological and pharmacological importance. For example, the sought-after product retinal can be obtained in a simple manner by reacting a trans-3-methyl-but-2-ene-1,4-dial-1-acetal with the ylide of a β-ionylideneethyl-triphenylphosphonium salt and subsequent hydrolysis. Retinal has the same activity as vitamin A. Furthermore, β-carotin can be prepared very economically from retinal by a simple Wittig reaction with the retinyltriphenylphosphonium salt easily obtainable from retinol.

Various methods of preparation of trans-3-methyl-but-2-ene-1,4-dial-1-acetals are known.

For example, German Laid-Open Application DOS No. 2,225,612 describes their preparation by oxidizing cyclic 3-methyl-but-2-en-4-ol-1-al-acetals in acetone by means of a solution of chromic acid in sulfuric acid. This process takes place with relatively good yields. However, its industrial implementation is made very difficult by the use of chromic acid as the oxidant and by the severe effluent problems presented by the toxicity of chromium compounds.

German Laid-Open Application DOS No. 2,357,752 discloses the preparation of the desired trans-3-methyl-but-2-ene-1,4-dial-1-acetals by oxidizing the corresponding 3-methyl-but-2-en-1-al-acetals with selenium oxide in certain solvents. In this process, the yields achieved are unsatisfactory. Furthermore, the high toxicity of selenium presents great problems when carrying out the process industrially.

Further, German Laid-Open Application DOS No. 2,513,999 discloses the preparation of trans-3-methyl-but-2-ene-1,4-dial-1-acetals from crotonaldehyde-acetals by ozonolysis followed by reductive working-up, Grignard vinylation and acetylation of the resulting glyoxalmonoacetals, hydroformylation of the resulting novel 2-acetoxy-but-3-en-1-al-acetals and elimination of acetic acid. However, the numerous and in part expensive steps which this process requires entail relatively high manufacturing costs.

It is an object of the present invention to provide a process which permits preparation of the sought-after trans-3-methyl-but-2-ene-1,4-dial-1-acetals in a technically particularly simple manner, ie. with minimum labor requirement.

The 3-chloro-3-methyl-butane-1,4-dial-bis-acetals (Ia) and 3-methyl-but-2-ene-1,4-dial-bis-acetals (Ib) which we have found are novel compounds through which the sought-after trans-3-methyl-but-2-ene-1,4-dial-1-acetals can be obtained in an industrially particularly advantageous manner since, on the one hand, the novel compounds can be prepared industrially in a very simple and cheap manner from readily obtainable starting materials, whilst on the other hand they can be converted in a very simple manner into the trans-3-methyl-but-2-ene-1,4-dial-1-acetals.

The novel chlorobutanedial-bis-acetals and butenedial-bis-acetals of the general formula I may be prepared by a method wherein A. a six-membered cyclic acetal of 3-methyl-but-3-en-1-al, of the general formula II

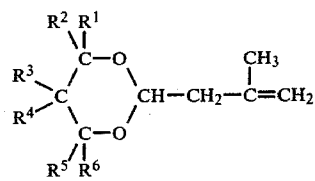

is reacted, in the presence of methanol and hydrochloric acid, and in the presence or absence of a solvent which is inert under the reaction conditions, with nitrosyl chloride or a nitrite ester of the general formula III $$R^7-O-N=O \quad (III)$$

where $R^7$ is alkyl of 1 to 6 carbon atoms, especially methyl, ethyl or isopropyl, to give a compound of the formula I, where Y is —H and X is Cl (Ia) and, if desired, B. hydrogen chloride is eliminated from this compound by a conventional method.

It is very surprising that on reacting an acetal of the formula II with nitrosyl chloride or an alkyl nitrite in the presence of methanol and HCl, tha novel 2-chloro-2-methyl-butane-1,4-dial-bis-acetals can be obtained in yields of up to 80% (at a conversion of about 50%), since it is known from U.S. Pat. No. 3,671,590 that on reacting an olefin with an organic nitrite in the presence of an acid catalyst, a cleavage of the double bond of the olefin, similar to ozonolysis, in general occurs.

The invention further relates to the use of the novel chlorobutanedial-bis-acetals and butenedial-bis-acetals of the general formula I for the preparation of 3-methyl-fumarodialdehyde-1-monoacetals of the general formula IV

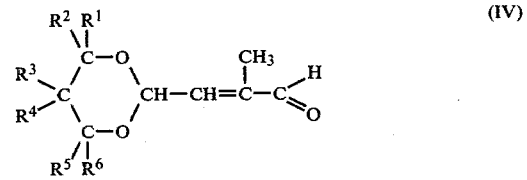

where $R^1$ to $R^6$ have the above meanings, by treating the novel butenedial-bis-acetals of the general formula Ib

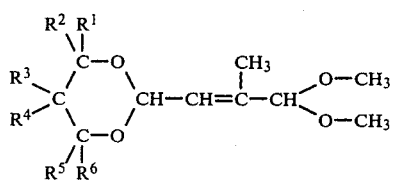

with a dilute aqueous acid.

The invention further relates to a process for the preparation of 3-methyl-fumarodialdehyde-1-monoacetals of the general formula IV

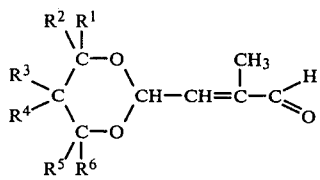

where $R^1$ to $R^6$ have the above meanings, wherein

A. a six-membered cyclic acetal of 3-methyl-but-3-en-1-al, of the general formula II

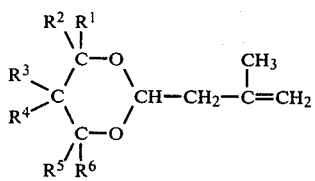

is reacted, in the presence of methanol and hydrochloric acid and in the presence or absence of a solvent which is inert under the reaction conditions, with nitrosyl chloride or a nitrite ester of the general formula III

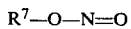

$$R^7-O-N=O \quad\quad (III)$$

where $R^7$ is alkyl of 1 to 6 carbon atoms, especially methyl, ethyl or isopropyl, B. hydrogen chloride is eliminated by a conventional method from the resulting novel chlorobutanedial-bis-acetals of the general formula Ia

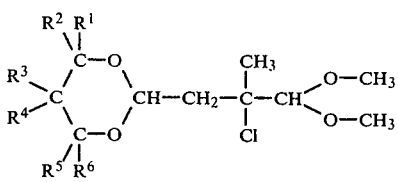

where $R^1$ to $R^6$ have the above meanings, and

C. the resulting butenedial-bis-acetals (methyl-fumarodialdehyde-bis-acetals) of the general formula Ib

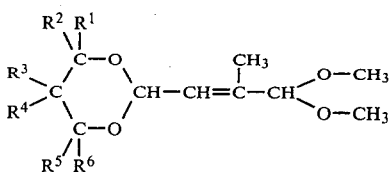

are partially hydrolyzed by treatment with a dilute aqueous acid.

The six-membered cyclic acetals of 3-methyl-but-3-en-1-al required as starting materials II can be obtained in a simple manner by acetalizing 3-methyl-but-3-en-1al, which in turn can be prepared by oxidative dehydrogenation of 3-methyl-but-3-en-1-ol in the presence of a mixed catalyst of, for example, silver and/or copper and metal oxides (compare German Pat. No. 2,243,810). 3-Methyl-but-3-en-1-ol, for its part, can easily be prepared by reacting isobutylene with formaldehyde.

Examples of suitable starting materials II are the acetals of 3-methyl-but-3-en-1-al with the diols propane-1,3-diol, butane-1,3-diol, pentane-2,4-diol, 2,2-dimethyl-propane-1,3-diol and 2-methyl-propane-1,3-diol. Acetals which may be singled out as being particularly suitable are those of 3-methyl-but-3-en-1-al with 2,2-dimethyl-propane-1,3-diol and 2-methylpropane-1,3-diol, namely 3-methyl-but-3en-1-al-(2',2'-dimethyl-1,3-propylene)-acetal and 3-methyl-but-3-en-1-al-(2'-methyl-1,3-propylene)-acetal.

The conversion of the starting compounds II to the chlorobutanedial-bis-acetals may be carried out with nitrosyl chloride or with a nitrite ester. The reaction takes place in a particularly advantageous manner if methyl nitrite is used.

The hydrogen chloride is in general first introduced into the reactor as a solution of HCl gas in methanol, or is passed, as HCl gas, into the reaction mixture. If concentrated aqueous HCl solutions are used, substantially poorer yields are achieved.

The molar ratios in which the reactants are employed can vary within wide limits. In general, from 5 to 20 moles, preferably from 12 to 16 moles, of methanol, from 1 to 3.5 moles, preferably from about 2 to 2.5 moles, of nitrosyl chloride or alkyl nitrite, and from about 0.5 to 3.0 moles, preferably from 1.0 to 2.0 moles, of hydrogen chloride are used per mole of acetal of the formula II.

The reaction is in general carried out without the use of additional solvents, since the methanol serves as the solvent. If solvents are added, it is advantageous to use those which are inert toward the nitrosylating agent and toward HCl, for example aliphatic, cycloaliphatic or aromatic hydrocarbons or halohydrocarbons.

The reaction is in general carried out at from $-10°$ C. to $70°$ C., preferably from $0°$ to $25°$ C. The reaction time is in general from about 30 minutes to 2 hours. The reaction is in general carried out under atmospheric pressure, but can also be carried out advantageously under superatmospheric pressure, for example under a pressure of up to 10 atmospheres.

The reaction can be carried out batchwise or continuously. In batchwise operation, it is advantageous to introduce the nitrosylating agent and a solution of HCl in methanol into a solution of the starting compound II in methanol, at the rate at which the reaction proceeds. In continuous operation a suitable method is, for example, to introduce the reactants and the catalyst continuously into a reaction vessel equipped with an overflow.

In principle, the reaction mixture can be worked up in the usual manner by distillation. Advantageously, the hydrogen chloride is neutralized with a base before the distillation. The acetal formed, of the formula Ia, can also be isolated after removing the solvent, for example by extracting the reaction mixture, to which water has been added, with a water-immiscible solvent, for example benzene or methylene chloride, and then distilling the organic phase. To prepare 3-methyl-but-2-ene-1,4-dial-bis-acetals or 3-methyl-fumaraldehyde-1-monoacetals it is however advantageous directly to process further the reaction mixture obtained from reaction A, without removing unconverted II and only then to remove unconverted starting material and any by-products formed.

The elimination of HCl from the compound Ia, to form the corresponding compound Ib, is advantageously effected with a strong base such as NaOH, KOH, sodium alkanolates or potassium alkanolates, in a solvent, advantageously in an alkanol. Solutions of NaOH, KOH, NaOCH$_3$, KOCH$_3$, NaOC$_2$H$_5$, KOC$_2$H$_5$, K-O-tert-C$_4$H$_9$ or Na-O-tert-C$_4$H$_9$ in the corresponding alkanols are particularly suitable.

The strong bases are in general employed in amounts of 1.5 moles per mole of Ia and the alcohols in amounts of from about 5 to 10 moles per mole of Ia. The reaction time is in general from 30 minutes to 6 hours, preferably from 60 to 120 minutes; the reaction temperature is in general from 0° to 100° C., preferably from 50° to 100° C., depending on the nature of the strong base and of the solvent.

The reaction mixture is worked up in the conventional manner by distilation. The yield of the desired product Ib is, surprisingly, about 80% of theory.

For further details of the elimination of hydrogen halide from alkyl halides, reference may be made to Houben-Weyl, "Methoden der Organischen Chemie", volume 5/1B, pages 134 et seq.

The sought-after 3-methyl-fumarodialdehyde-1-acetals can easily be prepared from the butenedial-bis-acetals of the general formula Ib by acid hydrolysis.

The acid hydrolysis is carried out in the conventional manner by treatment with an aqueous mineral acid, eg. sulfuric acid or hydrochloric acid, or with an organic acid, eg. formic acid, p-toluenesulfonic acid or acetic acid in the form of a solution of from 1 to 20% strength, the treatment being carried out with thorough mixing. The reaction time is in general from 0.5 to 5, preferably from 2 to 3, hours and the reaction temperature is from about 10° to 50° C.

It is advisable to add a solubilizing agent to the reaction mixture when carrying out the hydrolysis. Particularly suitable solubilizing agents are lower aliphatic alcohols, eg. methanol, ethanol and propanol, and cyloaliphatic ethers, eg. tetrahydrofuran and dioxane. The aldehydes obtained can be isolated in the conventional manner, for example by extracting the reaction mixture after it has been gently neutralized (for example with an alkali metal bicarbonate or sodium carbonate), and distilling off the extractant.

Whilst during this acid hydrolysis the dimethylacetal group in the $\alpha$-position to the methyl group hydrolyzes rapidly, the six-membered cyclic acetal group, surprisingly, remains unattacked, as during the acid treatment of the acetals of the formula II in process step A. In contrast, the six-membered cyclic acetal group in other unsaturated aldehydes is easily hydrolyzable. If, for example, a 3-methyl-fumarodialdehyde-1-acetal obtained according to the invention is reacted, in a Wittig reaction, with the ylide of a $\beta$-ionylidene-ethyl-triphenyl-phosphonium salt, the six-membered cyclic acetal of retinal is obtained, and the acetal group of this compound can easily be cleaved under the above hydrolysis conditions. This opens up numerous possibilities of arriving, by successive Wittig reactions with the 3-methyl-fumarodialdehyde-1-monoacetals, at various compounds of biological and pharmacological importance.

The 3-chloro-3methyl-butane-1,4-dial-bis-acetals and 3-methyl-but-2-ene-1,4-dial-bis-acetals which we have found are novel compounds through which the 3-methyl-fumarodialdehyde-1-monoacetals, which are sought-after compounds for terpene syntheses, can be obtained industrially in a particularly advantageous manner.

EXAMPLE 1

A. Preparation of
3-methyl-3-chlorobutane-1,4-dial-4-dimethylacetal-1-[2',2'-dimethyl-propylene]-acetal 17 g (0.1 mole) of 3-methyl-but-3en-1-al -[2',2'-dimethylpropylene]-acetal and 15 ml of methyl alcohol were together cooled to 0°. 16 ml of isopropyl nitrite and a solution of 9 g of HCl in 24 ml of methyl alcohol were simultaneously added dropwise, in the course of 4 hours, to the above solution at 0° C. After completion of the addition, the reaction mixture was stirred for a further 10 minutes at the same temperature and was then neutralized by adding 30% strength sodium methanolate. It was then filtered and concentrated under reduced pressure. The crude product obtained was examined by gas chromatography. It contained 40.5% of 3-methyl-3-chlorobutane-1,4-dial-4-dimethylacetal-1-[2',2'-dimethylpropylene]-acetal in addition to 46.5% of unconverted starting material and 13% of impurities. The yield, based on converted starting material, was 75.7%. The crude material can either be distilled or be used directly for further conversion. Distillation of a reaction batch of the above type gives pure product boiling at 98°–100° C./0.2 mbar and having the following NMR-spectroscopic data: $^1$H-NMR (solvent:CDCl$_3$; $\delta$ in ppm; TMS as an internal standard) $\delta$=4.75 (t, 1H); 4.20 (S, 1H); 3.5 (m4H+6H); 2.15 (d, 2H); 1.5 (s, 3H); 1.15 (s, 3H); 0.70 (s, 3H).

B. Preparation of
3-methyl-but-2-ene-1,4-dial-4-dimethylacetal-1-[2',2'-dimethylpropylene]-acetal 100 ml of a 30% strength sodium methanolate solution were added to the crude material obtained as described in Example 1A and the reaction mixture was refluxed for 3 hours. The mixture obtained was examined by gas chromatography. The following was found: 88% of the 3-methyl-3-chlorobutane-1,4-dial-4-dimethylacetal-1-[2',2'-dimethylpropylene]-acetal formed in 1A had been converted to the desired olefin, and the remainder had been converted to double-bond isomers and by-products. This corresponds to a yield of 88%, based on chlorobutane employed. Distillation of this reaction mixture gave 10 g of 3-methyl-but-2-ene-1,4-dial-4-dimethylacetal-1-[2',2'-dimethylpropylene]-acetal boiling at 84° C./0.1 mbar.

C. Preparation of 3-methyl-but-2-ene-1,4-dial-1-[2',2'-dimethylpropylene]-monoacetal 10 g of the bis-acetal obtained in Example Ib were dissolved in 50 ml of methylene chloride and stirred, at room temperature, with 50 ml of 3% strength hydrochloric acid. After 2 hours, analysis by gas chromatography showed that all the starting material had reacted and had been converted quantitatively into 3-methyl-fumarodialdehyde-1-monoacetal.

EXAMPLE 2

A. 17 g (0.1 mole) of 3-methyl-but-3-en-1-al-[2',2'-dimethylpropylene]-acetal were dissolved in 20 ml of methyl alcohol. A solution of 12.2 g (0.2 mole) of methyl nitrite in 20 ml of methyl alcohol, and a solution of 10 g of HCl in 10 ml of methyl alcohol, were added simultaneously, in the course of 1 hour, to the above solution at 0° C. After completion of the addition, the mixture was stirred for a further 30 minutes at 0° C. and was then neutralized with 30% strength sodium methanolate in methanol. Analysis of the reaction mixture by gas chromatography indicated a yield of 3-methyl-3-chlorobutane-1,4-dial-4-dimethylacetal-1[2',2'-dimethylpropylene]-acetal of 78% of theory, the conversion being 71%. Working up the reaction mixture by distillation gave a pure product boiling at 92° C. /0.1 mbar, and having the following NMR-spectroscopic data: $^1$H—NMR (solvent: CDCl$_3$; $\delta$ in ppm; TMS as internal standard); $\delta$=4.75 (t, 1H); 4.20 (s, 1H), 3.3–3.6 (m, 6H); 2.1 (d, 2H); 1.5 (s, 3H); 1.15 (s, 3H); 0.70 (s, 3H).

B. Elimination of HCl by means of sodium tert.-butanolate:

10 g of pure chlorobutane obtained in Example 2A were dissolved in 100 ml of tert-butanol, 3 g of sodium hydroxide powder were added and the reaction mixture was refluxed for 4 hours whilst stirring. After the reaction mixture had cooled, it was neutralized with acetic acid, the precipitate formed was filtered off and the filtrate was concentrated under reduced pressure. 9.1 g of an oily residue, containing—according to gas-chromatographic analysis—81.4% of the desired 3-methyl-but-2-ene-1,4-dial-4-dimethylacetal-1-[2',2'-dimethylpropylene]-acetal, were obtained. Subsequent distillation under greatly reduced pressure gave 6.24 g of the desired butenedial-bis-acetal boiling at 78° C./0.1 mbar; according to gas-chromatographic analysis, this product was 96% pure.

We claim:

1. Chlorobutanedial-bis-acetals and butenedial-bis-acetals of the formula I

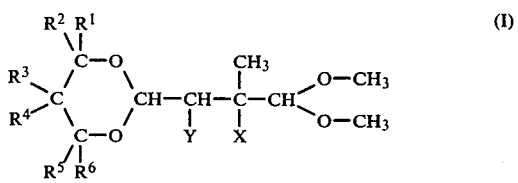

where $R^1$ to $R^6$ are H, —CH$_3$ or —C$_2$H$_5$ and Y is H if X is Cl (Ia) or Y and X together are a further bond between the carbon atoms bearing Y and X (Ib).

2. Bis-acetals as set forth in claim 1, wherein $R^1$ to $R^6$ are H or —CH$_3$.

3. Bis-acetals as set forth in claim 2, wherein from 1 to 4 of the radicals $R^1$ to $R^6$ are —CH$_3$ and the remainder are —H.

* * * * *